United States Patent [19]

Vaartstra

[11] Patent Number: 5,326,892

[45] Date of Patent: Jul. 5, 1994

[54] BIMETALLIC ALKOXIDE REAGENTS AND METHOD OF MAKING THE SAME

[75] Inventor: Brian A. Vaartstra, Bethel, Conn.

[73] Assignee: Advanced Technology Materials, Inc., Danbury, Conn.

[21] Appl. No.: 980,762

[22] Filed: Nov. 24, 1992

[51] Int. Cl.$^5$ .................... C07F 7/24; C07F 7/28
[52] U.S. Cl. ........................................ 556/28
[58] Field of Search ........................................ 556/28

[56] References Cited

PUBLICATIONS

"Metal Alkoxide Solutions for Advanced Ceramics", Chemat Technology, Inc., Product Catalog 1991.
Hampden-Smith et al., Ceram. Trans., vol. 25 (Ferroelect. Films), pp. 187–194 (1992).
"Metal Alkoxide Solutions for Advanced Ceramics", Chemat Technology, Inc., Product Catalog 1992.
Kwak et al., J. Appl. Phys., vol. 69, No. 2, pp. 767–772 (1991).
Brierly et al., Ferroelectrics, vol. 91, pp. 181–192 (1989).
Okamura et al., Japan. J. Appl. Phys., vol. B30, pp. 1034–1037 (1991).
Fukui et al., J. Mater. Res., vol. 7, pp. 791–794 (1992).
Athar et al., Synth. React. Inorg. Met-Org. Chem., vol. 19, No. 2, pp. 195–206 (1989).
Ramamurthi et al., Mat. Res. Soc. Symp. Proc. 180, pp. 79–84 (1990).
Kezuka et al., J. Am. Ceram. Soc., vol. 72, No. 9, pp. 1660–1663 (1989).
Sogani et al., Main Group Metal Chemistry, vol. 13, No. 6, pp. 375–386 (1990).

*Primary Examiner*—José Dees
*Assistant Examiner*—Porfirio Nazario
*Attorney, Agent, or Firm*—Janet Elliott

[57] ABSTRACT

Bimetallic alkoxide compounds useful as source reagents for chemical vapor deposition of ferroelectric ceramics such as lead titanate and lead zirconate, and lead zirconate titanate (PZT). The novel bimetallic alkoxide compounds of the present invention have the formula $R^1{}_xPbM(OR^2)_y(OR^3)_z$ (1) or $R^1{}_xPbOM(OR^2)_y(OR^3)_z$ (2), wherein M is a Group IVB metal, especially titanium or zirconium, and $R^1$, $R^2$, and $R^3$ are independently selected hydrocarbyls, especially C1–C6 alkyls. In these compounds, lead may be present in the +2 or +4 oxidation states. For compound 1, when lead is in the +2 oxidation state, x may be 0, 1 or 2, y and z range from 0 to 4, and $x+y+z=6$. When lead is present in the +4 oxidation state, x may range from 0 to 3, y and z range from 0 to 6, and $x+y+z=8$. For compound 2, when lead is in the +2 oxidation state, x may be 0, 1 or 2, y and z range from 0 to 4, and $x+y+z=4$. When lead is present in the +4 oxidation state, x may range from 0 to 3, y and z range from 0 to 4, and $x+y+z=6$. For 1 and 2, $R^1$, $R^2$, and $R^3$ are hydrocarbyl groups such as alkyl, cycloalkyl, alkenyl or aryl. $R^1$ is preferably methyl, ethyl, propyl, cyclopentadienyl, or methylcyclopentadienyl, and most preferably methyl or ethyl. $R^2$ and $R^3$ are preferably t-butyl, s-butyl, i-propyl, cyclohexyl, or neopentyl, and most preferably t-butyl or s-butyl.

15 Claims, 1 Drawing Sheet

BIMETALLIC ALKOXIDE REAGENTS AND METHOD OF MAKING THE SAME

GOVERNMENT RIGHTS IN INVENTION

This invention was made with Government support under Contract No. DASG60-92-C-0025 awarded by the U.S. Army. The Government has certain rights in this invention.

BACKGROUND OF THE INVENTION

1. Field of the Invention

This invention relates to bimetallic alkoxide compounds useful as source reagents or precursors in chemical vapor deposition (CVD) processes such as those employed in the fabrication of ferroelectric and other oxide thin films.

2. Description of the Related Art

Ceramic materials have a wide range of useful properties, including optical transparency, semiconductivity, and superconductivity. Ferroelectric ceramic materials are especially interesting because of their high piezoelectric coefficients, high opto-electronic coefficients, high dielectric constants and high pyroelectric constants. Lead zirconate titanate (PZT) is an attractive ferroelectric capacitor material because of its large spontaneous polarization, low coercive field and high mechanical strength. It has also been well studied because of its extensive use in piezoelectric transducers.

Because of their great potential in microelectronics applications, thin film growth techniques for ferroelectrics such as PZT are required. The primary growth techniques used to deposit high quality ferroelectric thin films have been rf sputtering (Kwak, B. S.; Zhang, K.; Boyd, E. P.; Erbil, A.; Wilkens, B. J. J. Appl. Phys. 1991, 69 767) and metalorganic deposition (MOD). The latter involves thermal decomposition of soluble precursors from a solution phase. The high temperature post annealing procedures required here are unacceptable in actual device manufacture. With sputtering, as-deposited films have high coercive fields and low remnant polarizations and again require high temperature annealing to achieve good FE properties. High temperature annealing steps cannot be used in device processing schemes where the already formed structures would be destroyed by diffusion, for example, in a highly desirable application of ferroelectric thin films, as the dielectric elements in dynamic random access memories.

An alternative technique which has been very successful for semiconductor materials deposition is metal-organic chemical vapor deposition (MOCVD). The primary attraction of this technique is the potential for in-situ growth of the ferroelectric perovskite phase. Although more complicated than the MOD process, MOCVD is viewed as the technique that will ultimately be used for PZT device manufacture if the perovskite phase can be formed at temperatures compatible with other device materials (T<450° C.) and without the post anneal step, which is typically greater than 600° C. Preliminary reports on the use of plasma enhanced-MOCVD have indeed described in-situ growth of the perovskite phase below 500° C. Other advantages include the relatively simple scale-up to commercial production volumes as well as the superior step coverage of CVD.

The use of MOCVD for ferroelectric oxides has been limited by the lack of available metalorganic precursors and the toxicity associated with some of them (Brierley, C. J.; Trundle, C.; Considine, L.; Whatmore, R. W.; Ainger, F. W. Ferroelectrics 1989, 91, 181). While metal oxides have been successfully deposited using metal alkoxide precursors as an alternative to alkyls, there are only a few known for lead, and their volatilities are low.

The highest priority issue for MOCVD of complex oxides is control of stoichiometry. The conventional approach for compositional control over a quaternary oxide is to introduce metal-organic precursors to the reactor via three independently controlled manifolds, each requiring accurate control of temperature, pressure, flow rates and precursor concentrations. Besides its complexity, this method makes film stoichiometry highly sensitive to inaccuracies in any of these process variables.

In addition, problems are encountered in the preparation of the oxide ferroelectric materials in thin film form on diamond or other carbon-containing substrates. The methods for preparing these ferroelectric materials are well-known, including chemical vapor deposition, sputtering, and sol-gel processing. Sputtering is a preferred method (see e.g., "Epitaxial Growth and Electrical Properties of Ferroelectric $Pb(Zr_{0.9}Ti_{0.1})O_3$ Films by Reactive Sputtering," Japan. J. Appl. Phys. B30, 1034–1037 (1991)). The ferroelectric oxide films are typically sputtered in the presence of oxygen, and thus the diamond substrate is liable to be oxidized. Therefore, a method for applying the films under milder conditions is needed.

While volatile materials for ferroelectrics such as lead titanate and lead zirconate titanate (and related doped analogs) are available, no sources exist which incorporate lead and titanium (or zirconium) in the desired 1:1 ratio directly. Also for the bulk manufacture of these oxides by "sol-gel" techniques and other thin film applications involving spin-on methods, a molecular precursor having a fixed lead-to-titanium(zirconium) ratio is desirable.

In general, lead titanate, lead zirconate and PZT have been made by mixture of separate precursors containing each of the required elements (c.f. Fukui et. al. J. Mater. Res. 1992, 7, 791). No bimetallic molecular species are known which contain lead and zirconium or lead and titanium in a 1:1 ratio. Only a few compounds containing lead and another metal have been previously reported. Mehrotra et. al. (Synth. React. Inorg. Met.-Org. Chem. 1989, 19, 195) reported the compound $Pb[Sb(OR)_4]_2$. Two reports of compounds that have 1:1 ratios of lead and titanium have appeared. Ramamurthi and Payne (Mat. Res. Soc. Proc. 1990, 180, 79) have proposed a compound that is polymeric, containing lead and titanium in an alkoxide framework. Yamaguchi et. al. (J. Am. Ceram. Soc. 1989, 72, 1660, and references therein) have synthesized $PbTiO_2(OR)_2$ by reaction of lead acetate and tetrabutoxytitanium. However these substances are not molecular species that contain only one atom of each metal, but rather have more than one empirical formula unit in each molecular formula. In each case, the relatively involatile product is not well defined as to molecular weight and vapor transport properties and is therefore not suitable as a CVD source reagent.

Accordingly, it is an object of the present invention to provide heterobimetallic source reagents containing two metals in the appropriate stoichiometric ratio required for the preparation of ceramic oxide films. Such reagents are sufficiently volatile to be used in CVD processes and decompose to deposit the desired oxide at temperatures that are low enough to be compatible with semiconductor device materials and processes.

It is another object of the present invention to provide methods of making these heterobimetallic source reagents.

Other objects and advantages of the present invention will be more fully apparent from the ensuing disclosure and appended claims.

SUMMARY OF THE INVENTION

In one aspect, the present invention relates to bimetallic alkoxide compounds, comprising source reagents having a 1:1 ratio of lead and a Group IVB element. The general formula of these compounds is:

$$R^1{}_xPbM(OR^2)_y(OR^3)_z$$

where lead may be present in the +2 or +4 oxidation states. M is a Group IVB metal, preferably titanium or zirconium. When lead is in the +2 oxidation state, x may be 0, 1 or 2, y and z range from 0 to 4, and $x+y+z=6$. When lead is present in the +4 oxidation state, x may range from 0 to 3 and $x+y+z=8$. $R^1$, $R^2$, and $R^3$ are hydrocarbyl groups such as alkyl, cycloalkyl, alkenyl or aryl. $R^1$ is preferably methyl, ethyl, propyl, cyclopentadienyl, or methylcyclopentadienyl, and most preferably methyl or ethyl. $R^2$ and $R^3$ are preferably t-butyl, s-butyl, i-propyl, cyclohexyl, or neopentyl, and most preferably t-butyl or s-butyl.

In another aspect, the present invention relates to bimetallic oxoalkoxide compounds, comprising source reagents having a 1:1 ratio of lead and a Group IVB element. The general formula of these compounds is:

$$R^1{}_xPbOM(OR^2)_y(OR^3)_z$$

where lead may be present in the +2 or +4 oxidation states. M is a Group IVB metal, preferably titanium or zirconium. When lead is in the +2 oxidation state, x may be 0, 1 or 2, y and z range from 0 to 4, and $x+y+z=4$. When lead is present in the +4 oxidation state, x may range from 0 to 3 and $x+y+z=6$. $R^1$, $R^2$, and $R^3$ are hydrocarbyl groups such as alkyl, cycloalkyl, alkenyl or aryl. $R^1$ is preferably methyl, ethyl, propyl, cyclopentadienyl, or methylcyclopentadienyl, and most preferably methyl or ethyl. $R^2$ and $R^3$ are preferably t-butyl, s-butyl, i-propyl, cyclohexyl, or neopentyl, and most preferably t-butyl or s-butyl.

Generalized chemical equations that illustrate the synthetic methods that may be used to prepare the compounds of the present invention are:

Pb[N(SiMe$_3$)$_2$]$_2$+M(OR$^2$)$_4$+HOR$^3$→PbM(OR$^2$)$_4$(OR$^3$)$_2$+HN(SiMe$_3$)$_2$

R$^1{}_3$PbOR$^2$+M(OR$^3$)$_4$→R$^1{}_3$PbM(OR$^2$)(OR$^3$)$_4$

R$^1{}_3$PbOR$^2$+M(OR$^3$)$_4$→R$^1{}_3$PbOM(OR$^2$)(OR$^3$)$_2$

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
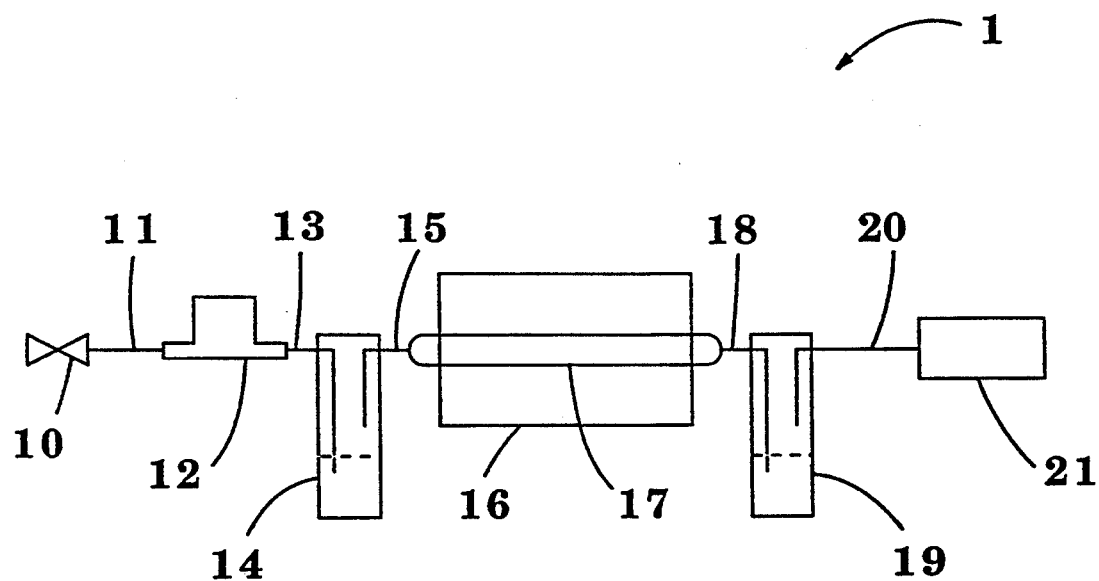
FIG. 1 is a schematic representation of a CVD system useful for deposition of oxide films using the reagents of the present invention.

The novel bimetallic alkoxide compounds of the present invention have the formulae $R^1{}_xPbM(OR^2)_y(OR^3)_z$ or $R^1{}_xPbOM(OR^2)_y(OR^3)_z$ wherein M is a Group IVB metal and $R^1$, $R^2$, and $R^3$ are hydrocarbyls. Of the IVB metals, titanium and zirconium are preferred. The hydrocarbyl groups $R^1$, $R^2$, and $R^3$ are selected to optimize the volatility of the bimetallic compounds for their intended use as CVD source reagents, and their precise identity is not critical to the invention. The hydrocarbyl groups may be alkyls, cycloalkyls, alkenyls, and aryls, with C1–C6 alkyl and cycloalkyl preferred.

For the alkoxide compound $R^1{}_xPbM(OR^2)_y(OR^3)_z$, lead may be present in the +2 or +4 oxidation state. When lead is in the +2 oxidation state, x may be 0, 1 or 2, y and z range from 0 to 4, and $x+y+z=6$. When lead is present in the +4 oxidation state, x may range from 0 to 3 and $x+y+z=8$. $R^1$, $R^2$, and $R^3$ are hydrocarbyl groups such as alkyl, cycloalkyl, alkenyl or aryl. $R^1$ is preferably methyl, ethyl, propyl, cyclopentadienyl, or methylcyclopentadienyl, and most preferably methyl or ethyl. $R^2$ and $R^3$ are preferably t-butyl, s-butyl, i-propyl, cyclohexyl, or neopentyl, and most preferably t-butyl or s-butyl.

For the oxoalkoxide compound $R^1{}_xPbOM(OR^2)_y(OR^3)_z$, lead may be present in the +2 or +4 oxidation state. When lead is in the +2 oxidation state, x may be 0, 1 or 2, y and z range from 0 to 4, and $x+y+z=4$. When lead is present in the +4 oxidation state, x may range from 0 to 3 and $x+y+z=6$. $R^1$, $R^2$, and $R^3$ are hydrocarbyl groups such as alkyl, cycloalkyl, alkenyl or aryl. $R^1$ is preferably methyl, ethyl, propyl, cyclopentadienyl, or methylcyclopentadienyl, and most preferably methyl or ethyl. $R^2$ and $R^3$ are preferably t-butyl, s-butyl, i-propyl, cyclohexyl, or neopentyl, and most preferably t-butyl or s-butyl.

The reagents may be synthesized by alcoholysis of a soluble Pb(II) amide in the presence of the Group IVB alkoxide, as exemplified by the preparative reaction shown below:

$$Pb[N(SiMe_3)_2]_2 + Zr(OtBu)_4 \xrightarrow{2HOtBu} PbZr(OtBu)_6 + 2HN(SiMe_3)_2$$

Bis(trimethylsilylamide) lead is useful as the lead amide in this reaction because it is soluble in the reaction medium, but other amides may be used as well.

The bimetallic alkoxide reagents may be prepared by means of reaction of the Group IVB alkoxide with an alkyllead alkoxide, as used to prepare the lead:titanium isopropoxy heterobimetallic compound:

$$Et_3PbOMe + Ti(OiPr)_4 \rightarrow Et_3PbOTi(OiPr)_3$$

Ceramic oxide thin films may be prepared using the bimetallic alkoxides of the present invention as source reagents in a CVD system, one example of which is shown in FIG. 1. Inert carrier gas, such as argon or nitrogen, enters the CVD system 1 through valve 10 and conduit 11. Mass flow controller 12 regulates the flow rate of the inert carrier gas, with the flow rate being selected to optimize the efficiency of source reagent conversion to thin film product. The inert carrier gas flows through conduit 13 into the source reagent reservoir 14, referred to as a "bubbler," which is heated to a temperature sufficient to volatilize source reagent into the carrier gas stream, typically in the range of 50°–250° C. The reagent-laden carrier gas stream flows through conduit 15 into the oven 16 where it contacts the substrate in chamber 17, which is heated to a temperature sufficient to promote source reagent decomposition, typically in the range 300°–500° C. The source reagent undergoes decomposition to deposit the ceramic oxide film upon a substrate, which may be any of a number of materials selected for their compatibility with the film and the intended application, such as silicon, magnesium oxide, alumina, silica, and the like. The gas stream, somewhat depleted of source reagent and containing volatile products of the decomposition, flows out of the chamber 17 via conduit 18 into liquid nitrogen-containing cold trap 19, which traps organic products of decomposition, and from whence via conduit 20 to pump 21, which exhausts the carrier gas stream.

The following non-limiting examples illustrate the preparation and use of the compounds of the present invention.

EXAMPLE 1

Synthesis of Et$_3$PbOTi(OiPr)$_3$

The compounds Et$_3$PbCl and Ti(OiPr)$_4$ were obtained commercially. Et$_3$PbOMe was prepared by reaction of Et$_3$PbCl and sodium methoxide. Et$_3$PbOMe (3 g) was loaded into a 100 mL flask in an inert atmosphere glove box. 25 mL of pentane added to the flask, and one equivalent of Ti(OiPr)$_4$ (2.7 mL) was added to the resulting suspension, which caused complete dissolution of the Et$_3$PbOMe. The reaction mixture was stirred for 4 hrs, and then the solvent was removed in vacuo leaving a colorless liquid. The colorless liquid product was vacuum distilled at about 160 mTorr using an external oil bath to heat the flask to about 50°. The distillate condensed at 35°–36° C. The yield of the liquid product was estimated at 70% based on volume.

The $^1$H NMR spectrum of the distillate in benzene-d$_6$ displayed no evidence for OMe groups. Resonances consistent with isopropoxide groups appeared at $\delta$4.44 (broad, 1H) and $\delta$1.28 (doublet, 6H). Resonances for ethyl groups on lead were spread over the region $\delta$1.0–2.0, with major peaks centered at $\delta$1.46 and $\delta$1.61. Elemental analysis: calcd for Et$_3$PbOTi(OiPr)$_3$, Pb, 38.7%; Ti, 8.9%; C, 33.6%; H, 6.8%. Found, Pb, 45.2%; Ti, 9.3%; C, 32.4%; H, 6.2%.

EXAMPLE 2

Synthesis of PbZr(OtBu)$_6$

A solution of Pb[N(SiMe$_3$)$_2$]$_2$ (2.0 g) in 20 mL of pentane was added to a solution of Zr(OtBu)$_4$ (1.48 mL) in 30 mL of pentane. t-Butanol (HOtBu) was added but no precipitation occurred until the solvent was reduced in volume. All solvent was removed in vacuo with slight warming to evolve the by-product HN(SiMe$_3$)$_2$. The solid product was recrystallized from pentane in 63% yield. $^1$H NMR of the crystallized material dissolved in CDCl$_3$ showed two resonances in a 1:1 ratio at $\delta$1.30 and $\delta$1.39. The crystalline product was sublimed at 150° C. and 150 mtorr, yielding a white powder. $^1$H NMR of this sublimate confirmed that the compound had sublimed unchanged. Elemental analysis: Calcd for PbZr(OtBu)$_6$: Pb, 28.1%; Zr, 12.4%; C, 39.1%; H, 7.4%. Found: Pb, 31.0%; Zr, 10.9%; C, 38.9%; H, 7.2%.

EXAMPLE 3

Deposition of PbTiO$_3$

Deposition was carried out in the CVD apparatus shown in FIG. 1. The liquid precursor Et$_3$PbOTi(OiPr)$_3$, synthesized as described in Example 1, was heated to 50° C. and an argon carrier gas flow of 10 sccm was initiated. Although the oven was set to a temperature of 550° C., the area of maximum deposition was found by separate thermocouple to be at 350° C. The thin film obtained was black in appearance. Analysis of peaks in the EDX spectrum of the film determined a 47.5:52.5 atomic ratio of lead to titanium. The volatiles that were trapped during the deposition were sampled by gas-tight syringe and injected into a GC/MS instrument. GC/MS analysis characterized the seven major constituents of the decomposition: ethylene, ethane, propylene, 2,3-dimethylbutane, butane, acetone, and isopropanol. All of these products are consistent with the composition of the precursor and can be explained based on decomposition mechanisms involving radical coupling or hydrogen transfer reactions.

EXAMPLE 4

Deposition of PbZrO$_3$

Deposition was carried out in the CVD apparatus shown in FIG. 1. The solid precursor compound PbZr(OtBu)$_6$, synthesized as described in Example 2, was heated to 150° C., and an argon carrier gas flow of 10 sccm was initiated. A dark deposit formed at the front of the furnace, at temperatures of approximately 300°–350°. The film was analyzed by EDX spectroscopy and was found to have a pronounced depth dependence of the atomic ratio Pb:Zr. Ratios of 25:75, 34:66, and 58:42 were determined at accelerating voltages of 10, 15, and 25 keV respectively.

While the invention has been described herein with reference to specific aspects, features, and embodiments, it will be apparent that other variations, modifications, and embodiments are possible, and all such variations, modifications, and embodiments therefore are to be regarded as being within the spirit and scope of the invention.

What is claimed is:

1. A bimetallic alkoxide compound having a 1:1 atomic ratio of lead and a Group IVB element and having formula R$^1{}_x$PbM(OR$^2$)$_y$(OR$^3$)$_z$; wherein
    M is a Group IVB metal;
    R$^1$, R$^2$, and R$^3$ are independently selected hydrocarbyl groups; and
    where lead may be present in the +2 or +4 oxidation states; and
    when lead is in the +2 oxidation state,
        x is [0,] 1 or 2;
        y and z range from 0 to 4; and
        x+y+z=6; and
    when lead is present in the +4 oxidation state,
        x ranges from [0] 1 to 3;
        y and z range from 0 to 6; and $x+y+z=8$.

2. A compound according to claim 1 wherein M is selected from the group consisting of titanium or zirconium.

3. A bimetallic alkoxide compound having a 1:1 atomic ratio of lead and a Group IVB element and having formula $R^1{}_xPbM(OR^2)_y(OR^3)_z$; wherein M is a Group IVB element selected from the group consisting of titanium or zirconium;

$R^1$ is selected from the group consisting of ethyl, methyl, propyl, cyclopentadienyl, and methylcyclopentadienyl, $R^2$ and $R^3$ are independently selected hydrocarbyl groups; and where lead may be present in the +2 or +4 oxidation states; and when lead is in the +2 oxidation state,
x is 1 or 2;
y and z range from 0 to 4; and
$x+y+z=6$; and when lead is present in the +4 oxidation state,
x ranges from 1 to 3;
y and z range from 0 to 6; and
$x+y+z=8$.

4. A compound according to claim 1, wherein $R^2$ and $R^3$ are independently selected from the group consisting of neopentyl, t-butyl, s-butyl, i-propyl, ethyl, and methyl.

5. A bimetallic oxoalkoxide compound having a 1:1 atomic ratio of lead and a Group IVB element and formula $R^1{}_xPbOM(OR^2)_y(OR^3)_z$; wherein M is a Group IVB metal;

$R^1$, $R^2$, and $R^3$ are independently selected hydrocarbyl groups; and where lead may be present in the +2 or +4 oxidation states; and when lead is in the +2 oxidation state,
x is 0, 1 or 2;
y and z range from 0 to 4; and
$x+y+z=4$; and when lead is present in the +4 oxidation state,
x ranges from 0 to 3;
y and z range from 0 to 6; and
$x+y+z=6$.

6. A compound according to claim 5 wherein M is selected from the group consisting of titanium or zirconium.

7. A compound according to claim 5, wherein $R^1$ is selected from the group consisting of ethyl, methyl, propyl, cyclopentadienyl, and methylcyclopentadienyl.

8. A compound according to claim 5, wherein $R^2$ and $R^3$ are independently selected from the group consisting of neopentyl, t-butyl, s-butyl, i-propyl, ethyl, and methyl.

9. A compound according to claim 8, wherein $R^1$ is ethyl and $R^2$ is isopropyl, x is 3, y is 3, and z is zero.

10. A compound according to claim 11, wherein M is titanium.

11. A bimetallic alkoxide compound having a 1:1 atomic ratio of lead and a Group IVB element and having formula $R^1{}_xPbM(OR^2)_y(OR^3)_z$; wherein M is a Group IVB metal;

$R^1$ is a hydrocarbyl group; and where $R^2$ and $R^3$ are independently selected from the group consisting of neopentyl, t-butyl, s-butyl, n-butyl, ethyl, and methyl; and where lead may be present in the +2 or +4 oxidation states; and when lead is in the +2 oxidation state,
x is 0, 1 or 2;
y and z range from 0 to 4; and
$x+y+z=6$; and when lead is present in the +4 oxidation state,
x ranges from 0 to 3;
y and z range from 0 to 6; and $x+y+z=8$.

12. A compound according to claim 11 wherein M is selected from the group consisting of titanium or zirconium.

13. A compound according to claim 11, wherein $R^1$ is selected from the group consisting of ethyl, methyl, propyl, cyclopentadienyl, and methylcyclopentadienyl.

14. A compound according to claim 14, wherein $R^2$ and $R^3$ are t-butyl, x is zero, and (y+z) is six.

15. A compound according to claim 14, wherein M is Zr.

* * * * *